United States Patent
Munn et al.

(10) Patent No.: US 6,946,172 B2
(45) Date of Patent: *Sep. 20, 2005

(54) RUBBERY PRODUCTS THAT SHRINK DUE TO THE APPLICATION OF ENERGY AND HYPO-ALLERGIC RUBBERY PRODUCTS

(75) Inventors: Charles S. Munn, 91 Walnut Hill Rd., Chestnut Hill, MA (US) 02467-3156; Robert E. Cohen, Jamaica Plain, MA (US)

(73) Assignee: Charles S. Munn, Chestnut Hill, MA (US)

( * ) Notice: Subject to any disclaimer, the term of this patent is extended or adjusted under 35 U.S.C. 154(b) by 65 days.

This patent is subject to a terminal disclaimer.

(21) Appl. No.: 09/761,468

(22) Filed: Jan. 16, 2001

(65) Prior Publication Data

US 2001/0012549 A1 Aug. 9, 2001

Related U.S. Application Data

(63) Continuation of application No. 08/907,100, filed on Aug. 6, 1997, now Pat. No. 6,221,447.
(60) Provisional application No. 60/054,051, filed on Jul. 31, 1997, provisional application No. 60/033,143, filed on Dec. 20, 1996, and provisional application No. 60/031,299, filed on Nov. 18, 1996.

(51) Int. Cl.[7] .................. B29D 22/00; B29D 23/00; B32B 1/08
(52) U.S. Cl. .................................................. 428/34.9
(58) Field of Search .............................. 428/34.9, 35.7, 428/36.8, 36.9; 2/161.7, 167, 168; 602/7, 42; 128/844; 215/11.1; 604/234, 235, 327; 433/136; 606/234; 156/85, 86; 264/289.3

(56) References Cited

U.S. PATENT DOCUMENTS

| | | | |
|---|---|---|---|
| 2,438,901 A | 4/1948 | Coxe | |
| 3,022,543 A | 2/1962 | Baird, Jr. et al. | |
| 3,129,996 A | 4/1964 | Locher | |

(Continued)

FOREIGN PATENT DOCUMENTS

| | | |
|---|---|---|
| DE | 29700260 U1 | 5/1989 |
| DE | 3817210 A1 | 11/1989 |

(Continued)

OTHER PUBLICATIONS

"No Such Thing as Safe Sex," The Oregonian, Nov. 23, 1991, p. B07.

English translation of Japanese Patent Appln. No. 2–297590, publishied JUn. 18, 1992.

'The New Demand for Shape–Memory Resins in Liquid Form,' Nikkei New Materials, pp. 64–68, Jul. 9, 1990 (accompanied by English translation).

Primary Examiner—Rena L. Dye
(74) Attorney, Agent, or Firm—Kriegsman & Kriegsman

(57) ABSTRACT

Rubbery products having a transition temperature that shrink from a second shape and size toward their original shape and size upon application of energy equivalent in result to raising the temperature of the rubbery product above the transition temperature. Also, hypo-allergenic rubbery products made from polybutadiene and its copolymers, trans-1,4-polybutadiene and its copolymers, synthetic isoprene and its copolymers, or synthetic cis-1,4-polyisoprene and its copolymers. Such rubbery products (not all of which need to be made to shrink) can be used in condoms, gloves, catheters, baby-bottle nipples, and dental dams, to name just a few.

7 Claims, 1 Drawing Sheet

U.S. PATENT DOCUMENTS

| | | | |
|---|---|---|---|
| 3,597,372 A | | 8/1971 | Cook |
| 3,639,917 A | * | 2/1972 | Althouse ................... 2/270 |
| 3,724,107 A | * | 4/1973 | Makinen et al. ............. 36/7.3 |
| 3,812,224 A | | 5/1974 | Smith et al. |
| 3,883,459 A | | 5/1975 | Kent |
| 4,187,360 A | | 2/1980 | Peters |
| 4,245,065 A | | 1/1981 | Peters |
| 4,596,728 A | | 6/1986 | Yang et al. |
| 4,728,290 A | | 3/1988 | Eisner et al. |
| 4,816,094 A | | 3/1989 | Pomplun et al. |
| 4,817,593 A | | 4/1989 | Taller et al. |
| 4,829,991 A | | 5/1989 | Boeck |
| 4,855,169 A | | 8/1989 | McGlothlin et al. |
| 4,869,723 A | | 9/1989 | Harmon |
| 4,891,409 A | | 1/1990 | Kuan et al. |
| 4,955,392 A | | 9/1990 | Sorkin |
| 4,964,416 A | | 10/1990 | Foldesy et al. |
| 4,981,147 A | | 1/1991 | Barnett |
| 5,014,361 A | | 5/1991 | Gray |
| 5,036,863 A | | 8/1991 | Wheeler |
| 5,094,250 A | | 3/1992 | Hessel |
| 5,112,900 A | | 5/1992 | Buddenhagen et al. |
| 5,176,152 A | | 1/1993 | Wheeler |
| 5,182,333 A | | 1/1993 | Powers et al. |
| 5,189,110 A | | 2/1993 | Ikematu et al. |
| 5,195,537 A | | 3/1993 | Tillotson |
| 5,199,444 A | | 4/1993 | Wheeler |
| 5,335,675 A | | 8/1994 | Wheeler, deceased et al. |
| 5,351,698 A | | 10/1994 | Wheeler, deceased et al. |
| 5,360,590 A | | 11/1994 | Wheeler |
| 5,391,343 A | | 2/1995 | Dreibelbis et al. |
| 5,399,400 A | * | 3/1995 | Nile et al. ................. 428/36.8 |
| 5,407,715 A | | 4/1995 | Buddenhagen et al. |
| 5,409,016 A | | 4/1995 | Bloodsaw |
| 5,458,936 A | | 10/1995 | Miller et al. |
| 5,469,863 A | | 11/1995 | Shah |
| 5,513,654 A | | 5/1996 | Delson |
| 5,526,823 A | | 6/1996 | Wheeler, deceased et al. |
| 5,563,241 A | * | 10/1996 | Beezhold ................... 528/482 |
| 5,658,526 A | | 8/1997 | Rastogi et al. |
| 5,799,333 A | | 9/1998 | McGarry et al. |
| 5,807,291 A | | 9/1998 | Larson et al. |
| 6,221,447 B1 | * | 4/2001 | Munn et al. ................ 428/34.9 |

FOREIGN PATENT DOCUMENTS

| | | |
|---|---|---|
| EP | 276128 | 7/1988 |
| EP | 668060 | 8/1995 |
| JP | 47-10494 | 5/1972 |
| JP | 48-14800 | 2/1973 |
| JP | 48-26941 | 8/1973 |
| JP | 50-146649 | 11/1975 |
| JP | 51-67380 | 6/1976 |
| JP | 60-259602 | 12/1985 |
| JP | 63-106414 | 7/1988 |
| JP | 64-46050 | 3/1989 |
| JP | 2-16031 | 1/1990 |
| JP | 3-18377 | 1/1991 |
| JP | 3-49767 | 3/1991 |
| JP | 4-170950 | 6/1992 |
| JP | 6-165794 | 6/1994 |
| JP | 6-269471 | 9/1994 |
| JP | 6-47069 | 11/1994 |
| JP | 7-276391 | 10/1995 |
| JP | 7-330023 | 12/1995 |
| JP | 8-81503 | 3/1996 |
| JP | 8-1188470 | 5/1996 |
| JP | 8-142272 | 6/1996 |
| WO | WO 86/04659 | 8/1986 |
| WO | WO 93/06795 | 4/1993 |

\* cited by examiner

RUBBERY PRODUCTS THAT SHRINK DUE TO THE APPLICATION OF ENERGY AND HYPO-ALLERGIC RUBBERY PRODUCTS

This application is a continuation of U.S. patent application Ser. No. 08/907,100, filed Aug. 6, 1997 now U.S. Pat. No. 6,221,447, which in turn claims the benefit of U.S. Provisional Application No. 60/031,299, filed Nov. 18, 1996, U.S. Provisional Application No. 60/033,143, filed Dec. 20, 1996, and U.S. Provisional Application No. 60/054,051, filed Jul. 31, 1997, the entire disclosures of which are hereby incorporated herein by reference.

TECHNICAL FIELD

The present invention relates to condoms, gloves, catheters, and other rubbery items, and in particular to condoms, gloves, catheters, and other rubbery items that are hypo-allergenic and/or can shrink when their temperature rises above a transition temperature.

BACKGROUND OF THE INVENTION

Condoms offer highly effective prevention against AIDS and other sexually transmitted diseases when used consistently and properly. However, condom purchase and use are limited by several factors, prominent among them being sexual dissatisfaction by the user and his partner, concern over impotence, allergic reaction, and occasional failures, such as falling off, even when used properly by experienced users. A snug fit during sexual activity would reduce occasional failures and provide for greater satisfaction. In addition, the application of some pressure against the penis by a snugly fitting condom may help to restrict venous blood return, in turn maintaining erection better or longer.

Also, there exists a great need for a variety of products to be made of a material similar to natural latex, but of absent or reduced allergenicity associated with latex derived from trees. Allergic contact dermatitis (Type-IV hypersensitivity reaction) from rubber products has long been recognized, but the rubbery polymer is rarely the sensitizer, rather the additives such as mercaptobenzothiazole and tetramethylthiuram are responsible.

Since 1979, many cases of immediate hypersensitivity (Type I) to natural latex rubber have been reported, including asthma, hives, and even death. The small amount of proteins and other natural tree products remaining in natural latex rubber are believed to be responsible.

Therefore, hypo-allergenic condoms and other products would be advantageous to those who might be allergic to conventional latex rubber. It is also advantageous that condoms have a snug fit during sexual activity, yet be easy to don before they are used for their intended purpose.

Condoms may also be used for non-sexual activities. For example, a condom may be combined with tubing in the manufacture and use of a condom-catheter in medical or home settings. In that case, it is also desirable that the condom be easy to don, yet have a snug fit when used as a condom-catheter. The induced adherence of the condom to the penis (due to its snug fit) could be far more comfortable and less traumatic to the skin of the penis than conventional designs (utilizing adhesives. etc.).

There are other applications for the use of items made of rubbery material that provide a snug or tight fit for the wearer or an instrument to be covered, and yet are easy to don. Examples are products that cover the tips or ends of a variety of objects and instruments, such as the transducer tip of an ultrasound machine's probe, gloves, finger cots, and oral-dental dams, to name just a few. With regard to gloves, medical and industrial gloves are likely to be preferred if they shrink to fit each user's hand, and perhaps even each portion of the hand, individually. This personalized fit may serve to encourage workers to use gloves as protection more often. Also, hypo-allergenic gloves would be advantageous often to those users who may be allergic to conventional latex rubber.

There is thus a need for condoms, gloves, catheters, and other rubber items that are easy to don yet provide a snug fit when used for their intended purposes, and/or are hypo-allergenic.

SUMMARY OF THE INVENTION

An embodiment of the present invention comprises rubbery material having a transition temperature that shrinks from a second shape and size toward a first (or original) shape and size upon application of energy equivalent in result to raising the temperature of the rubbery material above the transition temperature. The rubbery material may have a transition temperature in the range of 94 to 99 degrees Fahrenheit and be used in a condom. The rubbery material may also be used in a hand glove, a condom-catheter, and other similar items in which shrinkage is desired so that the item is easy to don or apply, yet shrinks to a snug fit.

A method for the manufacture and use of rubbery material having a transition temperature may comprise the following steps of: (i) manufacturing the rubbery material to a first shape and size which is cross-linked; (ii) after performing step (i), applying energy to the rubbery material, where the application of energy is equivalent in result to raising the rubbery material's temperature to at least the transition temperature; (iii) after performing step (i), stretching the rubbery material to a second shape and size; wherein steps (ii) and (iii) are performed in such a way that the rubbery material is in a state in which it is both in the second shape and size and its effective temperature is at least the transition temperature; and (iv) after steps (ii) and (iii) have been performed, reducing the effective temperature of the rubbery material below the transition temperature while the rubbery material is kept in the second shape and size, so that the rubbery material remains in the second shape and size, until subsequent application of energy to the rubbery material equivalent in result to raising its temperature to at least the transition temperature, whereupon the rubbery material shrinks from the second shape and size toward the first shape and size.

The above method may further comprise the step of applying energy to the rubbery material so that it shrinks from the second shape and size toward the first shape and size.

The rubbery material may comprise polybutadiene and its copolymers, polyurethane elastomers and their copolymers, trans pentenamer and its copolymers, ethylene pimelate and its copolymers, trans-1,4-polybutadiene and its copolymers, synthetic isoprene and its copolymers, or synthetic cis-1,4-polyisoprene and its copolymers.

Another embodiment of the invention comprises hypo-allergenic rubbery material. The rubbery material can be selected from the group consisting of polybutadiene and its copolymers, trans-1,4-polybutadiene and its copolymers, synthetic isoprene and its copolymers, and synthetic cis-1,4-polyisoprene and its copolymers. Such rubbery material can find uses in gloves, oral-dental dams, stretchy-bandages, baby-bottle nipples, pacifiers, catheters, tourniquets, dentist drains, injection ports for intravenous lines and catheters, and articles of clothing.

DETAILED DESCRIPTION OF SPECIFIC EMBODIMENTS

Figure 1:
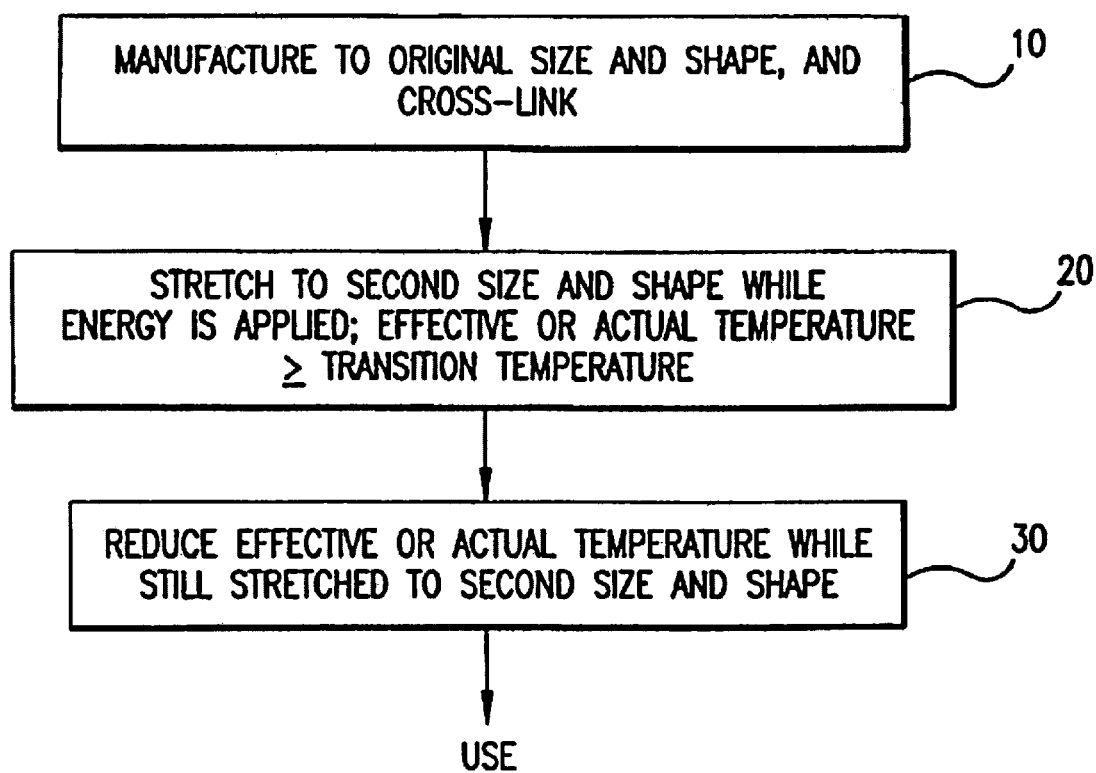
FIG. 1 is a flow diagram illustrating a method of manufacture for a condom, glove, catheter, or other similar rubbery device that shrinks due to the application of energy.

In step 10 of FIG. 1, the rubbery material forming part or all of the product is first cast, dipped, or otherwise formed into the shape and size that the product is to have after the final energy induced shrinkage is applied. We refer to this shape and size as the original shape and size (or the first shape and size) because the product is made to assume this shape and size during the initial step of FIG. 1.

For instance, in the case of a condom, the original shape and size would also be the final shape and size of the condom after unrestricted shrinkage by finally applied warmth during its use. Effectively, the condom or other product will "remember" this original shape and size, and during its subsequent use will return toward that original shape and size upon application of a sufficient amount of energy. In practice, the condom will be restricted from returning to its original shape and size because of the penis about which the condom is worn. However, the condom will fit snugly about the penis because it will at least return toward its original shape and size.

Unless otherwise stated or implied by context, the term "condom" is to encompass not only a conventional condom used for sexual activity, but also a condom-catheter or any other related device that makes use of a condom or condom-type article.

In step 10, the original shape and size is fixed by a subsequent chemical cross-linking step which may be activated by any of a variety of methods well known in the art of manufacturing elastomeric products. The cross-linking must be performed below the material's transition (melting) temperature. These cross-linking methods may use chemical cross-linking agents such as peroxides and/or sulfur. Alternatively, high energy radiation (for example, electrons) could be employed to cross-link the preformed rubbery product. The cross-linking renders the original shape and size of the object to be the equilibrium condition toward which the material will return at later stages when the energy-induced shrinkage is elicited.

In step 20, the rubbery material is stretched to the shape and size desired for its initial actual use. We refer to this new shape and size as the second shape and size, although it may be the first that the consumer encounters. For example, the second shape and size could be the shape and size of a condom just out of the package or just donned, prior to the application of warmth that occurs upon entering a partner in the case of sexual activity, or prior to the application of warmth or other energy by some other means in the case of a condom-catheter.

In step 20, the rubbery material must be brought into a state in which it is both (i) in the second shape and size and (ii) at a higher energy state than in step 10. The higher energy state is accomplished by applying energy to the rubbery material. This applied energy must be effectively equivalent in result to heating the rubbery material to a temperature equal to or above its transition (melting) temperature. That is, its effective temperature must be raised to at least its transition temperature. The energy can be in various forms, such as heat or electromagnetic radiation, for example. For example, a condom or other product could be stretched while in a warm bath to a temperature at or just above its transition (melting) point.

The second shape and size defines a temporary, non-equilibrium condition of deformity when compared to the original (first shape and size), equilibrium state. The rubbery material would rapidly return itself to the original shape and size were it not for step 30.

In step 30, while the rubbery material is still stretched, the application of energy to the rubbery material must be discontinued or lowered so as to have a result effectively equivalent to the rubbery material cooling to a temperature below its transition (melting) temperature. For example, a stretched condom or other product could be raised out of a warm bath and, while still stretched, lowered into a cool bath. This quenching process effectively seals the new, stretched shape and size into the product by aligning molecules into a particular arrangement. The rubbery material will now remain stretched until activated. However, the rubbery material still "remembers" the original shape and size.

Finally, after steps 10 through 30 of FIG. 1 have been performed, when the temperature of the rubbery material reaches the transition or melting temperature again, or when energy is applied so that the transition (melting) temperature is effectively reached again, this time during use of the product, the product is activated to shrink back to or toward the original shape and size that it "remembers."

For example, suppose a condom is made of rubbery material with a transition temperature similar to human body temperature. Then, when the worn condom enters the man's partner, it would be warmed (inside by the penis, and outside by the partner's body) to the transition temperature. This warming would de-stabilize the previously "quenched" second shape and size of step 30, and cause the condom to seek its original shape and size. Essentially, the condom would have been activated by the heat to return to its equilibrium state. Thus, the condom would shrink around the penis to fit each man individually.

Condoms, gloves, catheters, and other products made of rubbery material can be made to fit snugly when used for their intended purposes and yet be easily donned or applied if they are made of a rubbery material manufactured according to the method outlined in FIG. 1.

For example, for the case of condoms, the rubbery material of which they are composed may be manufactured so that when initially bought by a consumer the condom's diameter is relatively large and the transition temperature at which the condom shrinks in diameter is at or just below body temperature. Such transition temperature can be in the range of 94–99 degrees F. In this way, the condom is easy to don, and yet will provide a snug fit when worn by the user.

Similarly, gloves may be made so that after the manufacturing method of FIG. 1 but before their transition temperature is reached they are large relative to the wearer's hand, and so that after the transition temperature has been reached the gloves fit snugly. The transition temperature may be such that the gloves warm up to the transition temperature due to body heat alone, externally applied heat, special lighting, X-irradiation, or other methods of effectively heating an object.

Catheters and other rubbery devices that need to fit snugly and yet be easily donned can have similar properties as discussed above for condoms and gloves.

Possible rubbery compounds that may be used for the above discussed rubbery products are trans-1,4-polybutadiene and its copolymers, or polyurethane elastomers. For instance, the following rubbery compounds are expected to be able to be manufactured into condoms that would shrink at body temperature, after the wearer enters his partner or warmth is applied (as with warm air or water, for instance): trans polypentenamer, polyethylene pimelate, trans-1,4-polybutadiene, and some polyurethane elastomers, and some of the copolymers of any of them.

Likewise, one would choose other rubbery materials with the intention that they shrink in use in response to a higher or lower temperature, to special lighting, to X-irradiation, etc.

The amount and orientation of shrinkage are determined by the amount and orientation of stretching during the steps illustrated in FIG. 1. These can be varied (even widely) for various portions of the product. It is possible to manufacture a condom of such rubbery material and in such a way that it shrinks preferentially or even exclusively in diameter and circumference rather than in length. For instance, a condom for sexual use could be manufactured so that it is a bit large in diameter before donning, but shrinks in diameter after the man enters his partner. This would involve employing the method outlined in FIG. 1 where in step 20 the condom is stretched to increase mainly its diameter. Being a bit large to start with makes the condom easier to don.

Since the condom can be made so that it shrinks only a predetermined amount, it will not shrink too extensively. Thus, it will shrink to fit each man individually, affording a more comfortable fit and rendering the condom more likely not to slip off accidentally. For example, a condom could be manufactured so that during usage it will shrink in diameter 15% near the open end but only 8% elsewhere, but not at all in length. Rubber gloves, for example, could be made to shrink 10% at the fingers but only 5% at the central part of the hand and only 2% in length.

Some of these rubbery materials that shrink in response to the application of energy, and products that are made of them, can be manufactured to shrink at human body temperature (as during sexual intercourse). This involves choosing rubbery compounds with the desired transition temperature. For example, it was found that trans-1,4-polybutadiene is a rubbery material that has a transition temperature very close to 98.6 degrees Fahrenheit, which would make it a very desirable candidate to be used in a condom. Other rubbery products can be manufactured in relation to other temperatures. A variety of transition temperature choices allows for other uses of condoms and for uses other than condoms.

For instance, condoms that are not intended for sexual use may be manufactured as illustrated in FIG. 1. For example, a condom can be combined with tubing in the manufacture and use of a condom-catheter in medical or home settings. In that case, the shrinkage could occur at temperatures chosen in the manufacturing design to be at or other than at body temperature.

Similarly, products can be manufactured according to FIG. 1 that cover the tips or ends of a variety of objects and instruments in which a snug fit is obtained but in which it is desirable that the product can easily be applied over the object or instrument before shrinkage is induced. An example of such an object is the transducer tip of an ultrasound machine's probe. Other objects to be covered by the embodiments are fingers, in the case of gloves or finger cots, or the mouth, in the case of oral-dental dams. Thus, there are a variety of medical as well as non-medical applications for rubbery products made according to FIG. 1.

Shrinkage of the final rubbery product to its original shape and size can be accomplished by any means that raises temperature or effectively simulates the raising of temperature by applying energy, for example, heating or applying other kinds of energy, such as ultra-violet light, infrared light, electricity, X-irradiation, radioactive exposure, and applied pressure.

It has also been discovered that rubbery material made from polybutadiene and its copolymers, trans-1,4-polybutadiene and its copolymers, synthetic isoprene and its copolymers, or synthetic cis-1,4-polyisoprene and its copolymers, does not contain impurities that some users of natural latex rubber are allergic to. Therefore, regardless of whether the rubbery product is made according to the method outlined in FIG. 1, rubbery products made from these discussed materials are hypo-allergenic and may be used for such items as condoms, gloves, catheters, baby-bottle nipples, oral dental dams, stretchy bandages (e.g., bandages that wrap around or are pulled on), pacifiers, tourniquet, dentist drains, injection ports of intravenous lines or catheters, clothing employing elastic straps or bands, or any other rubbery items in physical or close contact with humans.

Some other embodiments of the present invention are products made of rubbery compounds that shrink at some transition temperature and are used as a wound covering and a surgical field delimiter and/or covering.

Other embodiments of the present invention can be made without departing from the scope or spirit of the invention.

We claim:

1. A glove comprising a rubbery material having a first shape and size, a second shape and size, and a transition temperature, wherein the rubbery material shrinks from the second shape and size toward the first shape and size after application of energy to the rubbery material where the application of energy is equivalent in result to raising the rubbery material's temperature to at least the transition temperature wherein the rubbery material comprises a substance selected from the group consisting of trans pentenamer and its copolymers, ethylene pimelate and its copolymers, trans-1,4-polybutadiene and its copolymers, and synthetic cis-1,4-polyisoprene and its copolymers.

2. The glove as set forth in claim 1, wherein the rubbery material consists essentially of synthetic cis-1,4-polyisoprene and its copolymers.

3. A glove made according to a method comprising the steps of:

(i) manufacturing and cross-linking a rubbery material having a transition temperature to a first shape and size, the rubbery material consisting essentially of a substance selected from the group consisting of trans pentenamer and its copolymers, ethylene pimelate and its copolymers, trans-1,4-polybutadiene and its copolymers, and synthetic cis-1,4-polyisoprene and its copolymers;

(ii) after performing step (i), applying energy to the rubbery material, where the application of energy is equivalent in result to raising the rubbery material's temperature to at least the transition temperature;

(iii) after performing step (i), stretching the rubbery material to a second shape and size; wherein steps (ii) and (iii) are performed in such a way that the rubbery material is in a state in which it is both in the second shape and size and its effective temperature is at least the transition temperature; and (iv) after steps (ii) and (iii) have been performed, reducing the effective temperature of the rubbery material below the transition temperature while the rubbery material is kept in the second shape and size so that the rubbery material remains in the second shape and size until subsequent application of energy to the rubbery material equivalent in result to raising its temperature to at least the transition temperature whereupon the rubbery material shrinks from the second shape and size toward the first shape and size.

4. A glove made according to a method comprising the steps of:
(i) manufacturing and cross-linking a rubbery material having a transition temperature to a first shape and size, the rubbery material consisting essentially of a substance selected from the group consisting of trans pentenamer and its copolymers, ethylene pimelate and its copolymers, trans-1,4-polybutadiene and its copolymers, and synthetic cis-1,4-polyisoprene and its copolymers;
(ii) after performing step (i), applying energy to the rubbery material, where the application of energy is equivalent in result to raising the rubbery material's temperature to at least the transition temperature;
(iii) after performing step (i), stretching the rubbery material to a second shape and size; wherein steps (ii) and (iii) are performed in such a way that the rubbery material is in a state in which it is both in the second shape and size and its effective temperature is at least the transition temperature;
(iv) after steps (ii) and (iii) have been performed, reducing the effective temperature of the rubbery material below the transition temperature while the rubbery material is kept in the second shape and size so that the rubbery material remains in the second shape and size until subsequent application of energy to the rubbery material equivalent in result to raising its temperature to at least the transition temperature whereupon the rubbery material shrinks from the second shape and size toward the first shape and size
(v) after step (iv), applying energy to the rubbery material so that it shrinks from the second shape and size toward the first shape and size.

5. A glove comprising a rubbery material having a transition temperature, said glove being made by a method comprising the steps of:
(i) manufacturing and cross-linking the rubbery material to a first shape and size, the rubbery material comprising a substance selected from the group consisting of trans pentenamer and its copolymers, ethylene pimelate and its copolymers, trans-1,4-polybutadiene and its copolymers, and synthetic cis-1,4-polyisoprene and its copolymers;
(ii) after performing step (i), applying energy to the rubbery material, where the application of energy is equivalent in result to raising the rubbery material's temperature to at least the transition temperature;
(iii) after performing step (i), stretching the rubbery material to a second shape and size, wherein steps (ii) and (iii) are performed in such a way that the rubbery material is in a state in which it is both in the second shape and size and its effective temperature is at least the transition temperature; and
(iv) after steps (ii) and (iii) have been performed, reducing the effective temperature of the rubbery material below the transition temperature while the rubbery material is kept in the second shape and size so that the rubbery material remains in the second shape and size until subsequent application of energy to the rubbery material equivalent in result to raising its temperature to at least the transition temperature whereupon the rubbery material shrinks from the second shape and size toward the first shape and size.

6. A rubber glove consisting essentially of a rubbery material having a first shape and size, a second shape and size, and a transition temperature, wherein the rubbery material shrinks from the second shape and size toward the first shape and size after application of energy to the rubbery material where the application of energy is equivalent in result to raising the rubbery material's temperature to at least the transition temperature wherein the rubbery material is a substance selected from the group consisting of polyurethane elastomers and their copolymers, trans pentenamer and its copolymers, ethylene pimelate and its copolymers, trans-1,4-polybutadiene and its copolymers, and synthetic cis-1,4-polyisoprene and its copolymers.

7. A glove made according to a method comprising the steps of:
(a) providing a rubbery material, said rubbery material consisting essentially of a substance selected from the group consisting of trans pentenamer and its copolymers, ethylene pimelate and its copolymers, trans-1,4-polybutadiene and its copolymers, and synthetic cis-1,4-polyisoprene and its copolymers;
(b) manufacturing the rubbery material to a first shape and size;
(c) after step (b), cross-linking the rubbery material, the cross-linked rubbery material having a transition temperature;
(d) after step (c), applying energy to the cross-linked rubbery material, where the application of energy is equivalent in result to raising the cross-linked rubbery material's temperature to at least the transition temperature;
(e) after step (b), stretching the cross-linked rubbery material to a second shape and size, wherein steps (d) and (e) are performed in such a way that the cross-linked rubbery material is in a state in which it is both in the second shape and size and its effective temperature is at least the transition temperature; and
(f) after steps (d) and (e), reducing the effective temperature of the cross-linked rubbery material below the transition temperature while the cross-linked rubbery material is kept in the second shape and size so that the cross-linked rubbery material remains in the second shape and size until subsequent application of energy to the cross-linked rubbery material equivalent in result to raising its temperature to at least the transition temperature whereupon the cross-linked rubbery material shrinks from the second shape and size toward the first shape and size.

* * * * *